(12) United States Patent
Schweikert et al.

(10) Patent No.: US 11,938,296 B2
(45) Date of Patent: *Mar. 26, 2024

(54) VENOUS ACCESS PORT WITH MOLDED AND/OR RADIOPAQUE INDICIA

(71) Applicant: Medical Components, Inc., Harleysville, PA (US)

(72) Inventors: Timothy M. Schweikert, West Chester, PA (US); Raymond R. Bizup, Feasterville, PA (US); Kevin E. Sanford, Chalfont, PA (US); Kenneth M. Zinn, Westport, CT (US)

(73) Assignee: Medical Components, Inc., Harleysville, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/865,449

(22) Filed: Jul. 15, 2022

(65) Prior Publication Data

US 2022/0347453 A1 Nov. 3, 2022

Related U.S. Application Data

(60) Continuation of application No. 16/035,879, filed on Jul. 16, 2018, now Pat. No. 11,406,808, which is a
(Continued)

(51) Int. Cl.
*A61M 39/02* (2006.01)
*A61M 5/00* (2006.01)

(52) U.S. Cl.
CPC ........ *A61M 39/0208* (2013.01); *A61M 5/007* (2013.01); *A61M 2039/0205* (2013.01);
(Continued)

(58) Field of Classification Search
CPC .............. A61M 39/0208; A61M 5/007; A61M 2039/0205; A61M 39/0229; A61M 39/0238; A61M 2205/32
See application file for complete search history.

(56) References Cited

U.S. PATENT DOCUMENTS

| 574,387 A | 12/1899 | Buckler |
| 611,357 A | 12/1899 | Dembinski |

(Continued)

FOREIGN PATENT DOCUMENTS

| DE | 8437873 U1 | 2/1986 |
| DE | 3447202 A1 | 7/1986 |

(Continued)

OTHER PUBLICATIONS

Boswell Declaration for U.S. Pat. No. 8,257,325, filed Sep. 4, 2012, 8 pages. (E6 Opposition / EP 2081634).

(Continued)

*Primary Examiner* — James D Ponton
*Assistant Examiner* — Hong-Van N Trinh

(57) ABSTRACT

A venous access port assembly having a base, a peripheral surface, and a septum. The base defines an interior reservoir. The peripheral surface includes integrally molded X-ray discernable indicia identifying that the assembly is rated for power injection. The X-ray discernable indicia may extend through a height of the peripheral surface from a top surface to a bottom surface thereof. According to one aspect, the peripheral surface may be formed from X-ray discernable material, and the X-ray discernable indicia may be formed from the X-ray discernable material, or they may be formed by voids in the X-ray discernable material. According to another aspect, the peripheral surface may be formed from a radiotransparent or radiolucent material and applied with a radiopaque agent, and the X-ray discernable indicia may be one or more voids in the radiopaque agent or may be portions of the peripheral surface applied with the radiopaque agent.

17 Claims, 5 Drawing Sheets

Related U.S. Application Data division of application No. 15/350,273, filed on Nov. 14, 2016, now Pat. No. 11,478,622, which is a continuation of application No. 13/550,745, filed on Jul. 17, 2012, now Pat. No. 9,533,133, which is a continuation of application No. 12/143,377, filed on Jun. 20, 2008, now Pat. No. 8,257,325.

(60) Provisional application No. 60/936,491, filed on Jun. 20, 2007.

(52) U.S. Cl.
CPC ........... *A61M 2039/0229* (2013.01); *A61M 2039/0238* (2013.01); *A61M 2205/32* (2013.01)

(56) References Cited

U.S. PATENT DOCUMENTS

| | | |
|---|---|---|
| 966,696 A | 8/1910 | Merrill |
| 1,713,267 A | 5/1929 | Crowley |
| 2,029,553 A | 2/1936 | Bartschi et al. |
| 2,433,480 A | 12/1947 | Rendich |
| 2,891,689 A | 6/1959 | Gould |
| D198,453 S | 6/1964 | Weichselbaum |
| 3,293,663 A | 12/1966 | Cronin |
| 3,341,417 A | 9/1967 | Sinaiko |
| 3,447,202 A | 6/1969 | Kato |
| 3,518,428 A | 6/1970 | Ring |
| 3,529,633 A | 9/1970 | Vaillancourt |
| 3,643,358 A | 2/1972 | Morderosian |
| 3,829,904 A | 8/1974 | Ling et al. |
| 3,831,583 A | 8/1974 | Edmunds, Jr. et al. |
| 3,840,009 A | 10/1974 | Michaels et al. |
| 3,891,997 A | 7/1975 | Herbert |
| 3,915,162 A | 10/1975 | Miller |
| 3,919,724 A | 11/1975 | Sanders et al. |
| 3,922,726 A | 12/1975 | Trentani et al. |
| 3,951,147 A | 4/1976 | Tucker et al. |
| 4,027,391 A | 6/1977 | Samis |
| 4,035,653 A | 7/1977 | Karasko |
| 4,121,108 A | 10/1978 | Manor |
| 4,123,806 A | 11/1978 | Amstutz et al. |
| 4,168,586 A | 9/1979 | Samis |
| 4,181,132 A | 1/1980 | Parks |
| 4,190,040 A | 2/1980 | Schulte |
| 4,190,057 A | 2/1980 | Downie et al. |
| 4,194,122 A | 3/1980 | Mitchell et al. |
| 4,202,349 A | 5/1980 | Jones |
| 4,222,374 A | 9/1980 | Sampson et al. |
| 4,233,964 A | 11/1980 | Jefferts et al. |
| 4,274,006 A | 6/1981 | Caine |
| 4,349,498 A | 9/1982 | Ellis et al. |
| 4,361,153 A | 11/1982 | Slocum et al. |
| 4,405,305 A | 9/1983 | Stephen et al. |
| 4,406,567 A | 9/1983 | Samis |
| 4,425,119 A | 1/1984 | Berglund |
| 4,445,896 A | 5/1984 | Gianturco |
| 4,450,592 A | 5/1984 | Niederer et al. |
| 4,450,985 A | 5/1984 | Beard |
| 4,456,011 A | 6/1984 | Warnecke |
| 4,469,483 A | 9/1984 | Becker et al. |
| 4,494,545 A | 1/1985 | Slocum et al. |
| 4,506,676 A | 3/1985 | Duska |
| 4,529,635 A | 7/1985 | Sheldon |
| 4,543,088 A | 9/1985 | Bootman et al. |
| 4,549,879 A | 10/1985 | Groshong et al. |
| 4,559,046 A | 12/1985 | Groshong et al. |
| 4,560,375 A | 12/1985 | Schulte et al. |
| 4,571,749 A | 2/1986 | Fischell |
| 4,576,595 A | 3/1986 | Aas et al. |
| 4,587,954 A | 5/1986 | Haber |
| 4,612,877 A | 9/1986 | Hayes et al. |
| 4,626,244 A | 12/1986 | Reinicke |
| 4,627,844 A | 12/1986 | Schmitt |
| 4,634,427 A | 1/1987 | Hannula et al. |
| 4,636,194 A | 1/1987 | Schulte et al. |
| 4,636,213 A | 1/1987 | Pakiam |
| 4,645,495 A | 2/1987 | Vaillancourt |
| 4,653,508 A | 3/1987 | Cosman |
| 4,655,765 A | 4/1987 | Swift |
| 4,657,024 A | 4/1987 | Coneys |
| 4,662,652 A | 5/1987 | Hargis |
| 4,668,221 A | 5/1987 | Luther |
| 4,671,796 A | 6/1987 | Groshong et al. |
| 4,673,394 A * | 6/1987 | Fenton, Jr. ........ A61M 39/0208 604/905 |
| 4,684,365 A | 8/1987 | Reinicke |
| 4,685,447 A | 8/1987 | Iversen et al. |
| 4,685,905 A | 8/1987 | Jeanneret |
| 4,692,146 A | 9/1987 | Hilger |
| 4,695,273 A | 9/1987 | Brown |
| 4,697,595 A | 10/1987 | Breyer et al. |
| 4,701,166 A | 10/1987 | Groshong et al. |
| 4,704,103 A | 11/1987 | Stoeber et al. |
| 4,710,174 A | 12/1987 | Moden et al. |
| 4,718,894 A | 1/1988 | Lazorthes |
| 4,728,894 A | 3/1988 | Yoda et al. |
| 4,743,231 A | 5/1988 | Kay et al. |
| 4,753,640 A | 6/1988 | Nichols et al. |
| 4,755,173 A | 7/1988 | Konopka et al. |
| 4,760,837 A | 8/1988 | Petit |
| 4,762,517 A | 8/1988 | Mcintyre et al. |
| 4,767,410 A | 8/1988 | Moden et al. |
| 4,772,270 A | 9/1988 | Wiita et al. |
| 4,772,276 A | 9/1988 | Wiita et al. |
| 4,773,552 A | 9/1988 | Boege et al. |
| 4,778,452 A | 10/1988 | Moden et al. |
| 4,781,680 A | 11/1988 | Redmond et al. |
| 4,781,685 A | 11/1988 | Lehmann et al. |
| 4,781,695 A | 11/1988 | Dalton |
| 4,802,885 A | 2/1989 | Weeks et al. |
| 4,804,054 A | 2/1989 | Howson et al. |
| 4,820,273 A | 4/1989 | Reinicke |
| 4,822,341 A | 4/1989 | Colone |
| 4,840,615 A | 6/1989 | Hancock et al. |
| 4,848,346 A | 7/1989 | Crawford |
| 4,857,053 A | 8/1989 | Dalton |
| 4,861,341 A | 8/1989 | Woodburn |
| 4,863,470 A | 9/1989 | Carter |
| 4,886,501 A | 12/1989 | Johnston et al. |
| 4,892,518 A | 1/1990 | Cupp et al. |
| 4,904,241 A | 2/1990 | Bark |
| 4,905,709 A | 3/1990 | Bieganski et al. |
| 4,909,250 A | 3/1990 | Smith |
| 4,915,690 A | 4/1990 | Cone et al. |
| 4,928,298 A | 5/1990 | Tanaka |
| 4,929,236 A | 5/1990 | Sampson |
| 4,955,861 A | 9/1990 | Enegren et al. |
| 4,963,133 A | 10/1990 | Whipple |
| 4,966,583 A | 10/1990 | Debbas |
| 4,973,319 A | 11/1990 | Melsky |
| 4,983,162 A | 1/1991 | Metais et al. |
| 5,002,735 A | 3/1991 | Alberhasky et al. |
| 5,009,644 A | 4/1991 | Mcdonald |
| 5,013,298 A | 5/1991 | Moden et al. |
| 5,041,098 A | 8/1991 | Loiterman et al. |
| 5,044,955 A | 9/1991 | Jagmin |
| 5,045,060 A | 9/1991 | Melsky et al. |
| 5,045,064 A | 9/1991 | Idriss |
| 5,084,015 A | 1/1992 | Moriuchi |
| 5,085,216 A | 2/1992 | Henley, Jr. et al. |
| 5,090,066 A | 2/1992 | Schoepe et al. |
| 5,092,849 A | 3/1992 | Sampson |
| 5,108,317 A | 4/1992 | Beinhaur et al. |
| 5,108,377 A | 4/1992 | Cone et al. |
| 5,112,301 A | 5/1992 | Fenton, Jr. et al. |
| 5,112,303 A | 5/1992 | Pudenz et al. |
| 5,129,891 A | 7/1992 | Young |
| 5,137,529 A | 8/1992 | Watson et al. |
| 5,147,483 A | 9/1992 | Melsky et al. |
| 5,152,753 A | 10/1992 | Laguette et al. |
| 5,156,600 A | 10/1992 | Young |

(56) References Cited

U.S. PATENT DOCUMENTS

| | | |
|---|---|---|
| 5,158,547 A | 10/1992 | Doan et al. |
| 5,167,629 A | 12/1992 | Vertenstein et al. |
| 5,167,633 A | 12/1992 | Mann et al. |
| 5,167,638 A | 12/1992 | Felix et al. |
| 5,171,228 A | 12/1992 | Mcdonald |
| 5,176,653 A | 1/1993 | Metals |
| 5,176,662 A | 1/1993 | Bartholomew et al. |
| 5,178,612 A | 1/1993 | Fenton, Jr. |
| 5,185,003 A | 2/1993 | Brethauer |
| 5,189,690 A | 2/1993 | Samuel |
| 5,193,106 A | 3/1993 | Desena |
| 5,195,122 A | 3/1993 | Fabian |
| 5,195,123 A | 3/1993 | Clement |
| 5,201,715 A | 4/1993 | Masters |
| 5,203,771 A | 4/1993 | Melker et al. |
| 5,203,777 A | 4/1993 | Lee |
| 5,213,574 A | 5/1993 | Tucker |
| 5,215,537 A | 6/1993 | Lynn et al. |
| 5,222,499 A | 6/1993 | Allen et al. |
| D337,637 S | 7/1993 | Tucker |
| 5,224,938 A | 7/1993 | Fenton, Jr. |
| 5,263,930 A | 11/1993 | Ensminger |
| 5,281,205 A | 1/1994 | Mcpherson |
| 5,290,263 A | 3/1994 | Wigness et al. |
| 5,295,658 A | 3/1994 | Atkinson et al. |
| 5,299,253 A | 3/1994 | Wessels |
| 5,309,863 A | 5/1994 | Leeb, Jr. |
| 5,312,337 A | 5/1994 | Flaherty et al. |
| 5,318,545 A | 6/1994 | Tucker |
| 5,320,100 A | 6/1994 | Herweck et al. |
| 5,322,511 A | 6/1994 | Armbruster et al. |
| 5,328,480 A | 7/1994 | Melker et al. |
| 5,332,398 A | 7/1994 | Miller et al. |
| 5,334,153 A | 8/1994 | Mcintyre et al. |
| 5,336,194 A | 8/1994 | Polaschegg et al. |
| 5,338,398 A | 8/1994 | Szwejkowski et al. |
| 5,350,360 A | 9/1994 | Ensminger et al. |
| 5,352,204 A | 10/1994 | Ensminger |
| 5,360,407 A | 11/1994 | Leonard et al. |
| 5,383,233 A | 1/1995 | Russell |
| 5,383,858 A | 1/1995 | Reilly et al. |
| D355,240 S | 2/1995 | Gladfelter et al. |
| 5,387,192 A | 2/1995 | Glantz et al. |
| 5,394,457 A | 2/1995 | Leibinger et al. |
| 5,395,324 A | 3/1995 | Hinrichs et al. |
| 5,397,329 A | 3/1995 | Allen |
| 5,399,168 A * | 3/1995 | Wadsworth, Jr. ............ A61M 39/0208 604/539 |
| 5,405,402 A | 4/1995 | Dye et al. |
| 5,417,565 A | 5/1995 | Long |
| 5,417,656 A | 5/1995 | Ensminger et al. |
| 5,421,814 A | 6/1995 | Geary |
| 5,423,334 A | 6/1995 | Jordan |
| 5,425,762 A | 6/1995 | Muller |
| 5,429,617 A | 7/1995 | Hammersmark et al. |
| 5,433,480 A | 7/1995 | Gresham et al. |
| 5,456,698 A | 10/1995 | Byland et al. |
| 5,476,460 A | 12/1995 | Montalvo |
| 5,476,880 A | 12/1995 | Cooke et al. |
| 5,484,402 A | 1/1996 | Saravia et al. |
| 5,503,630 A | 4/1996 | Ensminger et al. |
| 5,507,813 A | 4/1996 | Dowd et al. |
| 5,509,805 A | 4/1996 | Jagmin |
| 5,513,637 A | 5/1996 | Twiss et al. |
| 5,514,103 A | 5/1996 | Srisathapat et al. |
| 5,520,632 A | 5/1996 | Leveen et al. |
| 5,527,277 A | 6/1996 | Ensminger et al. |
| 5,527,307 A | 6/1996 | Srisathapat et al. |
| 5,531,684 A | 7/1996 | Ensminger et al. |
| 5,556,381 A | 9/1996 | Ensminger et al. |
| 5,558,641 A | 9/1996 | Glantz et al. |
| 5,562,617 A | 10/1996 | Finch, Jr. et al. |
| 5,562,618 A | 10/1996 | Cai et al. |
| 5,575,770 A | 11/1996 | Melsky et al. |
| 5,607,393 A | 3/1997 | Ensminger et al. |
| 5,607,407 A | 3/1997 | Tolkoff et al. |
| 5,613,945 A | 3/1997 | Cai et al. |
| 5,620,419 A | 4/1997 | Lui et al. |
| 5,632,729 A | 5/1997 | Cai et al. |
| 5,637,102 A | 6/1997 | Tolkoff et al. |
| 5,638,832 A | 6/1997 | Singer et al. |
| 5,647,855 A | 7/1997 | Trooskin |
| 5,662,600 A | 9/1997 | Watson et al. |
| 5,662,612 A | 9/1997 | Niehoff |
| 5,676,146 A | 10/1997 | Scarborough |
| 5,695,490 A | 12/1997 | Flaherty et al. |
| 5,702,128 A | 12/1997 | Maxim et al. |
| 5,702,363 A | 12/1997 | Flaherty |
| 5,704,915 A | 1/1998 | Melsky et al. |
| 5,709,668 A | 1/1998 | Wacks |
| 5,713,844 A | 2/1998 | Peyman |
| 5,713,858 A | 2/1998 | Heruth et al. |
| 5,713,859 A | 2/1998 | Finch, Jr. et al. |
| 5,718,382 A | 2/1998 | Jaeger |
| 5,718,682 A | 2/1998 | Tucker |
| 5,725,507 A | 3/1998 | Petrick |
| 5,733,336 A | 3/1998 | Neuenfeldt et al. |
| 5,733,400 A | 3/1998 | Gore et al. |
| 5,741,228 A | 4/1998 | Lambrecht et al. |
| 5,743,873 A | 4/1998 | Cai et al. |
| 5,743,891 A | 4/1998 | Tolkoff et al. |
| 5,746,460 A | 5/1998 | Marohl et al. |
| 5,758,667 A | 6/1998 | Slettenmark |
| 5,769,823 A | 6/1998 | Otto |
| 5,773,552 A | 6/1998 | Hutchings et al. |
| 5,776,188 A | 7/1998 | Shepherd et al. |
| 5,792,104 A | 8/1998 | Speckman et al. |
| 5,792,116 A | 8/1998 | Berg et al. |
| 5,810,789 A | 9/1998 | Powers et al. |
| 5,824,071 A | 10/1998 | Nelson et al. |
| 5,830,172 A | 11/1998 | Leveen et al. |
| 5,833,654 A | 11/1998 | Powers et al. |
| 5,835,563 A | 11/1998 | Navab et al. |
| 5,836,935 A | 11/1998 | Ashton et al. |
| 5,840,063 A | 11/1998 | Flaherty |
| 5,843,069 A | 12/1998 | Butler et al. |
| 5,853,394 A | 12/1998 | Tolkoff et al. |
| 5,868,702 A | 2/1999 | Stevens et al. |
| 5,882,353 A | 3/1999 | Vanbeek et al. |
| 5,895,424 A | 4/1999 | Steele et al. |
| 5,906,596 A | 5/1999 | Tallarida |
| 5,908,414 A | 6/1999 | Otto et al. |
| 5,913,998 A | 6/1999 | Butler et al. |
| 5,916,263 A | 6/1999 | Goicoechea et al. |
| 5,919,160 A | 7/1999 | Sanfilippo, II |
| 5,925,017 A | 7/1999 | Kriesel et al. |
| 5,925,030 A | 7/1999 | Gross et al. |
| 5,928,197 A | 7/1999 | Niehoff |
| 5,931,829 A | 8/1999 | Burbank et al. |
| 5,935,084 A | 8/1999 | Southworth |
| 5,944,023 A | 8/1999 | Johnson et al. |
| 5,944,688 A | 8/1999 | Lois |
| 5,944,712 A | 8/1999 | Frassica et al. |
| 5,947,953 A | 9/1999 | Ash et al. |
| 5,951,512 A | 9/1999 | Dalton |
| 5,951,522 A | 9/1999 | Rosato et al. |
| 5,954,687 A | 9/1999 | Baudino |
| 5,957,890 A | 9/1999 | Mann et al. |
| 5,968,011 A | 10/1999 | Larsen et al. |
| 5,970,162 A | 10/1999 | Kawashima |
| 5,989,216 A | 11/1999 | Johnson et al. |
| 5,989,239 A | 11/1999 | Finch et al. |
| 5,997,524 A | 12/1999 | Burbank et al. |
| 6,007,516 A | 12/1999 | Burbank et al. |
| 6,013,051 A | 1/2000 | Nelson |
| 6,013,058 A | 1/2000 | Prosl et al. |
| 6,017,331 A | 1/2000 | Watts et al. |
| 6,022,335 A | 2/2000 | Ramadan |
| 6,033,389 A | 3/2000 | Cornish |
| 6,039,712 A | 3/2000 | Fogarty et al. |
| 6,077,756 A | 6/2000 | Lin et al. |
| 6,086,555 A | 7/2000 | Eliasen et al. |
| 6,090,066 A | 7/2000 | Schnell |

(56) References Cited

U.S. PATENT DOCUMENTS

| | | |
|---|---|---|
| 6,102,884 A | 8/2000 | Squitieri |
| 6,113,572 A | 9/2000 | Gailey et al. |
| 6,120,492 A | 9/2000 | Finch et al. |
| 6,161,033 A | 12/2000 | Kuhn |
| 6,171,198 B1 | 1/2001 | Lizama et al. |
| 6,171,298 B1 | 1/2001 | Matsuura et al. |
| 6,174,330 B1 | 1/2001 | Stinson |
| 6,190,352 B1 | 2/2001 | Haarala et al. |
| 6,193,684 B1 | 2/2001 | Burbank et al. |
| 6,198,807 B1 | 3/2001 | Desena |
| 6,203,570 B1 | 3/2001 | Baeke |
| 6,213,973 B1 | 4/2001 | Eliasen et al. |
| 6,228,088 B1 | 5/2001 | Miller et al. |
| 6,251,059 B1 | 6/2001 | Apple et al. |
| D445,175 S | 7/2001 | Bertheas |
| 6,269,148 B1 | 7/2001 | Jessop et al. |
| 6,287,293 B1 | 9/2001 | Jones et al. |
| 6,290,677 B1 | 9/2001 | Arai et al. |
| 6,302,875 B1 | 10/2001 | Makower et al. |
| 6,305,413 B1 | 10/2001 | Fischer et al. |
| D450,115 S | 11/2001 | Bertheas |
| 6,332,874 B1 | 12/2001 | Eliasen et al. |
| 6,347,241 B2 | 2/2002 | Burbank et al. |
| 6,355,021 B1 | 3/2002 | Nielsen et al. |
| 6,356,782 B1 | 3/2002 | Sirimanne et al. |
| 6,361,557 B1 | 3/2002 | Gittings et al. |
| 6,398,764 B1 | 6/2002 | Finch, Jr. et al. |
| 6,419,680 B1 | 7/2002 | Cosman et al. |
| 6,450,937 B1 | 9/2002 | Mercereau et al. |
| 6,459,772 B1 | 10/2002 | Wiedenhoefer et al. |
| 6,478,783 B1 | 11/2002 | Moorehead |
| 6,482,217 B1 | 11/2002 | Pintor et al. |
| 6,494,867 B1 | 12/2002 | Elver et al. |
| 6,497,062 B1 | 12/2002 | Koopman et al. |
| 6,500,155 B2 | 12/2002 | Sasso |
| 6,503,228 B1 | 1/2003 | Li et al. |
| 6,527,754 B1 | 3/2003 | Tallarida et al. |
| 6,537,255 B1 | 3/2003 | Raines |
| RE38,074 E | 4/2003 | Recinella et al. |
| 6,582,418 B1 | 6/2003 | Verbeek et al. |
| 6,613,002 B1 | 9/2003 | Clark et al. |
| 6,613,662 B2 | 9/2003 | Wark et al. |
| 6,626,936 B2 | 9/2003 | Stinson |
| 6,629,950 B1 | 10/2003 | Levin |
| 6,632,217 B2 | 10/2003 | Harper et al. |
| 6,652,486 B2 | 11/2003 | Bialecki et al. |
| 6,652,503 B1 | 11/2003 | Bradley |
| 6,676,633 B2 | 1/2004 | Smith et al. |
| 6,697,664 B2 | 2/2004 | Kienzle et al. |
| 6,705,316 B2 | 3/2004 | Blythe et al. |
| 6,719,721 B1 | 4/2004 | Okazaki et al. |
| 6,719,739 B2 | 4/2004 | Verbeek et al. |
| 6,738,531 B1 | 5/2004 | Funahashi |
| 6,755,842 B2 | 6/2004 | Kanner et al. |
| 6,758,841 B2 | 7/2004 | Haarala et al. |
| 6,767,356 B2 | 7/2004 | Kanner et al. |
| 6,784,783 B2 | 8/2004 | Scoggin et al. |
| 6,826,257 B2 | 11/2004 | Sayre et al. |
| 6,852,106 B2 | 2/2005 | Watson et al. |
| 6,878,136 B2 | 4/2005 | Fleury et al. |
| 6,878,137 B2 | 4/2005 | Benchetrit |
| 6,949,084 B2 | 9/2005 | Marggi et al. |
| 6,962,580 B2 | 11/2005 | Adams et al. |
| 6,994,315 B2 | 2/2006 | Ryan et al. |
| 6,997,914 B2 | 2/2006 | Smith et al. |
| 7,008,377 B2 | 3/2006 | Beane et al. |
| 7,008,412 B2 | 3/2006 | Maginot |
| 7,016,456 B2 | 3/2006 | Basu et al. |
| 7,018,361 B2 | 3/2006 | Gillespie, Jr. et al. |
| 7,044,942 B2 | 5/2006 | Jolly et al. |
| 7,056,316 B1 | 6/2006 | Burbank et al. |
| 7,070,591 B2 | 7/2006 | Adams et al. |
| 7,072,704 B2 | 7/2006 | Bucholz |
| 7,074,232 B2 | 7/2006 | Kanner et al. |
| 7,076,305 B2 | 7/2006 | Imran et al. |
| 7,083,593 B2 | 8/2006 | Stultz |
| 7,108,686 B2 | 9/2006 | Burke et al. |
| 7,123,690 B1 | 10/2006 | Brown et al. |
| 7,127,040 B2 | 10/2006 | Sayre et al. |
| 7,131,962 B1 | 11/2006 | Estabrook et al. |
| 7,140,769 B2 | 11/2006 | Kay |
| 7,191,011 B2 | 3/2007 | Cantlon |
| 7,198,631 B2 | 4/2007 | Kanner et al. |
| 7,214,207 B2 | 5/2007 | Lynch et al. |
| 7,214,215 B2 | 5/2007 | Heinzerling et al. |
| 7,223,257 B2 | 5/2007 | Shubayev et al. |
| 7,229,417 B2 | 6/2007 | Foerster et al. |
| 7,235,067 B2 | 6/2007 | Morris et al. |
| D546,440 S | 7/2007 | Burnside |
| 7,242,982 B2 | 7/2007 | Singhal et al. |
| 7,252,469 B2 | 8/2007 | Zaluzec et al. |
| 7,252,649 B2 | 8/2007 | Sherry |
| 7,261,705 B2 | 8/2007 | Edoga et al. |
| D554,253 S | 10/2007 | Kornerup |
| 7,275,682 B2 | 10/2007 | Excoffier et al. |
| 7,276,075 B1 | 10/2007 | Callas et al. |
| D556,153 S | 11/2007 | Burnside |
| 7,306,579 B2 | 12/2007 | Fujii |
| 7,311,702 B2 | 12/2007 | Tallarida et al. |
| 7,318,816 B2 | 1/2008 | Bobroff et al. |
| 7,318,818 B2 | 1/2008 | Yashiro et al. |
| 7,322,953 B2 | 1/2008 | Redinger |
| D562,443 S | 2/2008 | Zinn et al. |
| 7,331,130 B2 | 2/2008 | Schweikert |
| 7,331,948 B2 | 2/2008 | Skarda |
| 7,333,013 B2 | 2/2008 | Berger |
| D564,449 S | 3/2008 | Dewberry |
| 7,347,838 B2 | 3/2008 | Kulli |
| 7,347,843 B2 | 3/2008 | Adams et al. |
| 7,351,233 B2 | 4/2008 | Parks |
| 7,377,915 B2 | 5/2008 | Rasmussen et al. |
| D574,950 S | 8/2008 | Zawacki et al. |
| 7,413,564 B2 | 8/2008 | Morris et al. |
| D578,203 S | 10/2008 | Bizup |
| 7,445,614 B2 | 11/2008 | Bunodiere et al. |
| D582,032 S | 12/2008 | Bizup et al. |
| 7,465,847 B2 | 12/2008 | Fabian |
| D595,892 S | 7/2009 | Smith et al. |
| 7,563,025 B2 | 7/2009 | Kay |
| 7,648,517 B2 | 1/2010 | Makower et al. |
| D612,479 S | 3/2010 | Zawacki et al. |
| 7,713,251 B2 | 5/2010 | Tallarida et al. |
| 7,785,302 B2 | 8/2010 | Powers |
| 7,833,281 B2 | 11/2010 | Lehman et al. |
| 8,257,325 B2 | 9/2012 | Schweikert et al. |
| 10,052,470 B2 | 8/2018 | Powers et al. |
| 10,179,230 B2 | 1/2019 | Powers et al. |
| 10,183,157 B2 | 1/2019 | Powers et al. |
| 10,625,065 B2 | 4/2020 | Powers et al. |
| 2001/0016717 A1 | 8/2001 | Haarala et al. |
| 2001/0051766 A1 | 12/2001 | Gazdzinski |
| 2001/0053889 A1 | 12/2001 | Marggi et al. |
| 2001/0056266 A1 | 12/2001 | Tallarida et al. |
| 2002/0095205 A1 | 7/2002 | Edwin et al. |
| 2002/0138068 A1 | 9/2002 | Watson et al. |
| 2002/0173769 A1 | 11/2002 | Gray et al. |
| 2003/0010929 A1 | 1/2003 | Priewe et al. |
| 2003/0028173 A1 | 2/2003 | Forsberg |
| 2003/0130627 A1 | 7/2003 | Smith et al. |
| 2003/0139812 A1 | 7/2003 | Garcia et al. |
| 2003/0181878 A1 | 9/2003 | Tallarida et al. |
| 2003/0191452 A1 | 10/2003 | Meglin et al. |
| 2004/0002693 A1 | 1/2004 | Bright et al. |
| 2004/0006316 A1 | 1/2004 | Patton |
| 2004/0019356 A1 | 1/2004 | Fraser et al. |
| 2004/0020462 A1 | 2/2004 | Sauler et al. |
| 2004/0044306 A1 | 3/2004 | Lynch et al. |
| 2004/0052333 A1 | 3/2004 | Sayre et al. |
| 2004/0054352 A1 | 3/2004 | Adams et al. |
| 2004/0056266 A1 | 3/2004 | Suh et al. |
| 2004/0064110 A1 | 4/2004 | Forsell |
| 2004/0073196 A1 | 4/2004 | Adams et al. |
| 2004/0093069 A1 | 5/2004 | Priewe et al. |
| 2004/0106878 A1 | 6/2004 | Skujins et al. |

(56) References Cited

U.S. PATENT DOCUMENTS

| | | |
|---|---|---|
| 2004/0106891 A1 | 6/2004 | Langan et al. |
| 2004/0157952 A1 | 8/2004 | Soffiati et al. |
| 2004/0158207 A1 | 8/2004 | Hunn et al. |
| 2004/0167543 A1 | 8/2004 | Mazzocchi et al. |
| 2004/0176743 A1 | 9/2004 | Morris et al. |
| 2004/0199129 A1 | 10/2004 | Dimatteo |
| 2004/0199220 A1 | 10/2004 | Cantlon |
| 2004/0204692 A1 | 10/2004 | Eliasen |
| 2004/0225254 A1 | 11/2004 | Tanaka et al. |
| 2004/0254536 A1 | 12/2004 | Conlon et al. |
| 2004/0254537 A1 | 12/2004 | Conlon et al. |
| 2005/0049553 A1 | 3/2005 | Triplett et al. |
| 2005/0070875 A1 | 3/2005 | Kulessa |
| 2005/0075614 A1 | 4/2005 | Bunodiere et al. |
| 2005/0085723 A1 | 4/2005 | Huebner |
| 2005/0113806 A1 | 5/2005 | De et al. |
| 2005/0131352 A1 | 6/2005 | Conlon et al. |
| 2005/0148866 A1 | 7/2005 | Gunderson |
| 2005/0148956 A1 | 7/2005 | Conlon et al. |
| 2005/0148957 A1 | 7/2005 | Girard et al. |
| 2005/0152841 A1 | 7/2005 | Sayre et al. |
| 2005/0171502 A1 | 8/2005 | Daly et al. |
| 2005/0182857 A1 | 8/2005 | Kong |
| 2005/0209573 A1 | 9/2005 | Brugger et al. |
| 2005/0215874 A1 | 9/2005 | Wang et al. |
| 2005/0215876 A1 | 9/2005 | Chen et al. |
| 2005/0241203 A1 | 11/2005 | Lizotte et al. |
| 2005/0256451 A1 | 11/2005 | Adams et al. |
| 2005/0256500 A1 | 11/2005 | Fujii |
| 2005/0277899 A1 | 12/2005 | Conlon et al. |
| 2005/0283119 A1 | 12/2005 | Uth et al. |
| 2006/0009788 A1 | 1/2006 | Freeman et al. |
| 2006/0017341 A1 | 1/2006 | Hahn et al. |
| 2006/0084929 A1 | 4/2006 | Eliasen |
| 2006/0089619 A1 | 4/2006 | Ginggen |
| 2006/0100592 A1 | 5/2006 | Eliasen |
| 2006/0116648 A1 | 6/2006 | Hamatake |
| 2006/0173410 A1 | 8/2006 | Moberg et al. |
| 2006/0173424 A1 | 8/2006 | Conlon |
| 2006/0178647 A1* | 8/2006 | Stats ............... A61M 39/0208 604/288.01 |
| 2006/0184141 A1 | 8/2006 | Smith et al. |
| 2006/0184142 A1 | 8/2006 | Schon et al. |
| 2006/0217359 A1 | 9/2006 | Wentworth et al. |
| 2006/0217659 A1 | 9/2006 | Patton |
| 2006/0224128 A1 | 10/2006 | Lurvey et al. |
| 2006/0224129 A1 | 10/2006 | Beasley et al. |
| 2006/0247584 A1* | 11/2006 | Sheetz ............... A61B 6/032 604/288.02 |
| 2006/0253076 A1 | 11/2006 | Butts et al. |
| 2006/0264898 A1 | 11/2006 | Beasley et al. |
| 2007/0007839 A1 | 1/2007 | Lin |
| 2007/0049876 A1 | 3/2007 | Patton |
| 2007/0055290 A1 | 3/2007 | Lober |
| 2007/0073250 A1 | 3/2007 | Schneiter |
| 2007/0078391 A1 | 4/2007 | Wortley et al. |
| 2007/0078416 A1 | 4/2007 | Eliasen |
| 2007/0078432 A1 | 4/2007 | Halseth et al. |
| 2007/0083156 A1 | 4/2007 | Muto et al. |
| 2007/0149920 A1 | 6/2007 | Michels et al. |
| 2007/0149921 A1 | 6/2007 | Michels et al. |
| 2007/0161958 A1 | 7/2007 | Glenn |
| 2007/0161985 A1 | 7/2007 | Demakas et al. |
| 2007/0179456 A1 | 8/2007 | Glenn |
| 2007/0185462 A1 | 8/2007 | Byrum |
| 2007/0191773 A1 | 8/2007 | Wojcik |
| 2007/0208313 A1 | 9/2007 | Conlon et al. |
| 2007/0219510 A1 | 9/2007 | Zinn et al. |
| 2007/0233017 A1 | 10/2007 | Zinn et al. |
| 2007/0233018 A1 | 10/2007 | Bizup et al. |
| 2007/0255234 A1 | 11/2007 | Haase et al. |
| 2007/0270691 A1 | 11/2007 | Bailey et al. |
| 2007/0270770 A1 | 11/2007 | Bizup |
| 2007/0276344 A1 | 11/2007 | Bizup et al. |
| 2007/0299408 A1 | 12/2007 | Alferness et al. |
| 2008/0004642 A1 | 1/2008 | Birk et al. |
| 2008/0008654 A1 | 1/2008 | Clarke et al. |
| 2008/0015701 A1 | 1/2008 | Garcia et al. |
| 2008/0039820 A1 | 2/2008 | Sommers et al. |
| 2008/0048855 A1 | 2/2008 | Berger |
| 2008/0108949 A1 | 5/2008 | Beasley et al. |
| 2008/0114308 A1 | 5/2008 | Di et al. |
| 2008/0138387 A1 | 6/2008 | Machiraju |
| 2008/0140025 A1 | 6/2008 | Sheetz et al. |
| 2008/0208236 A1 | 8/2008 | Hobbs et al. |
| 2008/0281279 A1 | 11/2008 | Hoendervoogt et al. |
| 2008/0319398 A1 | 12/2008 | Bizup |
| 2008/0319399 A1 | 12/2008 | Schweikert et al. |
| 2008/0319405 A1 | 12/2008 | Bizup |
| 2009/0024024 A1 | 1/2009 | Zinn |
| 2009/0024098 A1 | 1/2009 | Bizup et al. |
| 2009/0035582 A1 | 2/2009 | Nakatani et al. |
| 2009/0118683 A1 | 5/2009 | Hanson et al. |
| 2009/0156928 A1 | 6/2009 | Evans et al. |
| 2009/0171436 A1 | 7/2009 | Casanova et al. |
| 2009/0204072 A1 | 8/2009 | Amin et al. |
| 2009/0204074 A1 | 8/2009 | Powers et al. |
| 2009/0221976 A1 | 9/2009 | Linden |
| 2009/0227862 A1 | 9/2009 | Smith et al. |
| 2009/0227951 A1 | 9/2009 | Powers et al. |
| 2010/0004735 A1 | 1/2010 | Yang et al. |
| 2010/0042073 A1 | 2/2010 | Oster et al. |
| 2010/0069743 A1 | 3/2010 | Sheetz et al. |
| 2019/0134373 A1 | 5/2019 | Barron et al. |
| 2019/0151641 A1 | 5/2019 | Powers et al. |
| 2019/0217073 A1 | 7/2019 | Maniar et al. |
| 2019/0252603 A1 | 8/2019 | Wiley et al. |
| 2019/0275311 A1 | 9/2019 | Hibdon et al. |
| 2020/0086105 A1 | 3/2020 | Powers et al. |

FOREIGN PATENT DOCUMENTS

| | | |
|---|---|---|
| DE | 19745654 A1 | 4/1999 |
| EP | 0619101 A1 | 10/1994 |
| EP | 0750520 B1 | 8/2000 |
| EP | 1238682 A2 | 9/2002 |
| EP | 1896117 B1 | 1/2011 |
| FR | 1509165 A | 1/1968 |
| FR | 2569987 A1 | 3/1986 |
| FR | 2586569 A1 | 3/1987 |
| GB | 2203342 A | 10/1988 |
| JP | 2500388 Y2 | 6/1996 |
| JP | H08-168322 A | 7/1996 |
| JP | 2602109 B2 | 4/1997 |
| JP | 2003-102831 A | 4/2003 |
| JP | 2004-350937 A | 12/2004 |
| JP | 2006-500087 A | 1/2006 |
| JP | 2006-025948 A | 2/2006 |
| WO | 86/00213 A1 | 1/1986 |
| WO | 93/05730 A1 | 4/1993 |
| WO | 95/14504 A1 | 6/1995 |
| WO | 97/01370 A1 | 1/1997 |
| WO | 97/06845 A1 | 2/1997 |
| WO | 97/11726 A1 | 4/1997 |
| WO | 98/17337 A1 | 4/1998 |
| WO | 99/42166 A1 | 8/1999 |
| WO | 00/33901 A1 | 6/2000 |
| WO | 00/47264 A1 | 8/2000 |
| WO | 02/47549 A1 | 6/2002 |
| WO | 02/100480 A2 | 12/2002 |
| WO | 03/037215 A2 | 5/2003 |
| WO | 03/086508 A1 | 10/2003 |
| WO | 2004/004800 A2 | 1/2004 |
| WO | 2004/071555 A2 | 8/2004 |
| WO | 2004/091434 A2 | 10/2004 |
| WO | 2005/037055 A2 | 4/2005 |
| WO | 2006/096686 A1 | 9/2006 |
| WO | 2006/116438 A2 | 11/2006 |
| WO | 2006/130133 A1 | 12/2006 |
| WO | 2006/134100 A1 | 12/2006 |
| WO | 2007/025266 A2 | 3/2007 |
| WO | 2007/079024 A2 | 7/2007 |
| WO | 2007/092210 A1 | 8/2007 |
| WO | 2007/094898 A2 | 8/2007 |

(56) References Cited

FOREIGN PATENT DOCUMENTS

| WO | 2006/078915 A3 | 9/2007 |
|---|---|---|
| WO | 2007/098771 A2 | 9/2007 |
| WO | 2007/109164 A2 | 9/2007 |
| WO | 2007/126645 A2 | 11/2007 |
| WO | 2007/136538 A2 | 11/2007 |
| WO | 2008/008126 A2 | 1/2008 |
| WO | 2008/019236 A1 | 2/2008 |
| WO | 2008/048361 A1 | 4/2008 |
| WO | 2008/063226 A2 | 5/2008 |
| WO | 2008/147760 A1 | 12/2008 |
| WO | 2008/157763 A1 | 12/2008 |
| WO | 2009/002839 A1 | 12/2008 |
| WO | 2009/012385 A1 | 1/2009 |
| WO | 2009/012395 A1 | 1/2009 |
| WO | 2009/035582 A1 | 3/2009 |
| WO | 2009/046439 A2 | 4/2009 |
| WO | 2009/046725 A1 | 4/2009 |
| WO | 2009/108669 A1 | 9/2009 |

OTHER PUBLICATIONS

Brochure for PowerPort, Feel the New Standard of Care, 4 pages. (D6 Opposition / EP 2081634).
Declaration of Kelly Christian, Director of Product Development at Bard Access Systems, Inc, in support of and depicting a product on the market by Quinton Company approximately ten years prior to Oct. 22, 2009, Oct. 22, 2009, 1 page.
Extravasation of Radiologic Contrast, PA-PSRS Patient Safety Advisory—vol. 1, No. 3, Sep. 2004, 6 pages.
Guidance for Industry and FDA Staff, Use of Symbols on Labels and in Labeling of In Vitro Diagnostic Devices Intended for Professional Use, Nov. 30, 2004, 12 pages.
Guidance on Medical Device Patient Labeling; Final Guidance for Industry and FDA Reviewers, Apr. 19, 2001, 54 pages.
Interference Decision for Patent Interference No. 105,860, declared on Nov. 10, 2011, 9 pages. (E5 Opposition / EP 2180915).
International Preliminary Examination Report Received for PCT Application No. PCT/US1999/028695, dated Apr. 21, 2001, 4 pages.
International Preliminary Report on Patentability and Writen Opinion Received for PCT Patent Application No. PCT/US2006/016056, dated Oct. 30, 2007, 9 pages.
International Preliminary Report on Patentability Received for PCT Application No. PCT/US2006/008022, dated Sep. 12, 2007, 6 pages.
International Preliminary Report on Patentability Received for PCT Application No. PCT/US2006/049007, dated Jul. 1, 2008, 5 pages.
International Preliminary Report on Patentability Received for PCT Application No. PCT/US2007/011015, dated Nov. 23, 2009, 9 pages.
International Preliminary Report on Patentability received for PCT Patent Application No. PCT/US2007/006776, dated Mar. 6, 2008, 3 pages.
International Search Report and Written Opinion received for International Patent Application No. PCT/US2012/050586, dated Oct. 22, 2012, 15 pages.
International Search Report and Written Opinion Received for PCT Application No. PCT/US2008/078976, dated Apr. 3, 2009, 6 pages.
International Search Report and Written Opinion received for PCT Patent Application No. PCT/US2008/070345, dated Dec. 1, 2008, 11 pages.
"IsoMed Constant-Flow Infusion System (Year: 2000)", 111 pages.
Notice of Opposition filed for European Patent Application No. 07753408.9 on Jul. 4, 2018, 24 pages.
Notice of Opposition filed for European Patent Application No. 08781983.5 on Jul. 4, 2018, 25 pages.
Patent Assignment recorded for U.S. Appl. No. 12/143,377, filed Aug. 4, 2008, 6 pages. (E4 Opposition / EP 2164559).

International Search Report and Written Opinion Received for PCT Patent Application No. PCT/US2006/49007, dated Oct. 1, 2007, 6 pages.
Port-A-Cath® "Implantable Epidural, Arterial and Peritoneal Access Systems," Internet Product Listing of Nov. 19, 2000 archived at http://web.archive.org/web/20001119035900/http://www.deltec.com/cPacspl.htm (2 pages).
U.S. Appl. No. 60/936,491, filed Jun. 20, 2007, 28 pages. (E2 Opposition / EP 2164559).
Reminders form FDA Regarding Ruptured Vascular Access Devices from Power Injection, Jul. 2004, 2 pages.
"Signs, Symbols, and Icons: Pre-history to the Computer Age", author: Rosemary Sassoon and Albertine Gaur, first published in 1997, 1997, 3 pages.
Transmittal letter and cover sheet for U.S. Appl. No. 60/658,518, filed Mar. 4, 2005, 2 pages. (E5 Opposition / EP 2164559).
U.S. Appl. No. 60/658,518, filed Mar. 4, 2005, 62 pages. (D2 Opposition / EP 2164559).
U.S. Appl. No. 60/675,309, filed Apr. 27, 2005, 100 pages.
U.S. Appl. No. 60/852,591, filed Oct. 18, 2006, 23 pages. (E2 Opposition / EP 2081634).
U.S. Appl. No. 60/961,133, filed Jul. 19, 2007, 24 pages. (E2 Opposition / EP 2180915).
"User Manual for the ESPrit 3G Apeech Processor and Accessories", Nucleus Cochlear Implant Systems; available at <http://www.cochlearamericas.com/PDFs/UserManualSprint.pdf>, Issue 2, Dec. 2001, 2 pages.
Notice of Opposition filed for European Patent Application No. 08771600.7, filed on Jul. 25, 2018, 26 pages.
Declaration of Interference Received for U.S. Appl. No. 11/725,287, filed Nov. 10, 2011, 6 pages.
Supplemental Response and Suggestion of Interference Filed for U.S. Appl. No. 11/725,287, filed Feb. 18, 2011, 64 pages.
Supplemental Response and Suggestion of Interference Filed for U.S. Appl. No. 11/725,287, filed May 26, 2011, 62 pages.
U.S. Appl. No. 60/658,518, filed Mar. 4, 2005, publicly accessible Oct. 5, 2006, 62 pages.
Bard Access System product drawings representative of the Bard Access System products on the market on or around Mar. 1995 as indicated by the Bard Access Systems Mar. 21, 1995 Product Release to Market form for "M.R.I. Port with 8 Fr. ChronoFlex Catheter," "M.R.I. Port with 8 Fr. ChronoFlex Catheter with Intro-Eze," "M.R.I. Port with 8 Fr. Chrono-Flex Catheter and Peel Apart," "M.R.I. Port with 8 Fr. ChronoFlex Catheter Demo Kit," 6 pages.
Extreme Access, Bard Access Systems, Inc., Product Brochure, 2003, 5 pages.
Bard Access Systems, Inc. "Hickman Subcutaneous Ports & Hickman/Broviac Catheters," Bard Exhibit 1017, p. 1-5, 1992.
Bard Access Systems, Inc., Extreme Access, "Ports—Setting the Standard with a Comprehensive Family of Ports," Bard Exhibit 1002, p. 1-17, 2003.
Bard Access Systems, Inc. "Power Port—Implantable Port—Feel the New Standard of Care—Guidelines for CT Technologists," Bard Exhibit 1004, p. 1, Feb. 2007.
Biffi, et al., "A Randomized, Prospective Trial of Central Venous Ports Connected to Standard Open-Ended or Groshong Catheters in Adult Oncology Patients." American Cancer Society, vol. 92, No. 5, pp. 1204-1212, Sep. 1, 2001, 9 pages.
Biffi, et al., "Best Choice of Central Venous Insertion Site for the Prevention of Catheter-Related Complications in Adult Patients Who Need Cancer Therapy: A Randomized Trial", Annals of Oncology, Jan. 29, 2009, 6 pages.
Biffi, et al., "Use of totally implantable central venous access ports for high-dose chemotherapy and peripheral blood stem cell transplantation: results of a monocentre series of 376 patients", Annals of Oncology, vol. 15, 2004, 5 pages.
BioEnterics® Lap-Band® "Adjustable Gastric Banding System" by !named Health, Product Brochure, Dec. 2003, 22 pages.
Lap-Band System Access Port Fill Guide I, "9.75/10.0 cm Lap-Band System vs. 11 cm Lap-Band System: For Product Manufactured Prior to Jul. 2001" BioEnterics Corporation, 1 page.

(56) References Cited

OTHER PUBLICATIONS

Carlson, et al., "Safety Considerations in the Power Injection of Contrast Media via Central Venous Catheters During Computed Tomographic Examinations", Investigative Radiology, vol. 27, No. 5, May 1992, pp. 337-340.
Costa, Nancy, "More Than Skin Deep: An Overview of Iodinated Contrast Media," Journal for the Association for Vascular Access, vol. 8, No. 4, 2003, 6 pages.
Costa, Nancy, "Understanding Contrast Media," Journal of Infusion Nursing, vol. 27, No. 5, Sep./Oct. 2004, 11 pages.
Coyle, et al., "Power Injection of Contrast Media via Peripherally Inserted Central Catheters for CT", The Journal of the Association for Vascular Access (JAVA), vol. 15, No. 8, Aug. 2004, pp. 809-814.
Port-A-Cath P.A.S. Port Systems by Deltec, Product Specifications, 1999, 2 pages.
Fallscheer, et al., "Injury to the Upper Extremity Caused by Extravasation of Contrast Medium: A True Emergency." Scandinavian Journal of Plastic and Reconstructive Surgery and Hand Surgery, vol. 41, pp. 26-32, 2007, 7 pages.
Herts, et al., "Power Injection of Contrast Media Using Central Venous Catheters: Feasibility, Safety and Efficacy", AJR:176(2), Feb. 2001, pp. 447-453.
Herts, et al., "Power Injection of Intravenous Contrast Material Through Central Venous Catheters for CT: In Vitro Evaluation", Radiology, vol. 200, No. 3, Sep. 1996, pp. 731-735.
Hou, et al., "Comparisons of Outcomes and Survivals for Two Central Venous Access Port Systems", Journal of Surgical Oncology, vol. 91, 2005, 6 pages.
Johnson, Kathleena, "Power Injectable Portal Systems", Journal of Radiology Nursing, vol. 28, Issue 1, Mar. 2009, 6 pages.
Lamaitre Vascular, "Port Implantations: using the OptiLock Implantable Port", product information, available at <http://www.lemaitre.com/specs_pop.asp>, Apr. 2003, 14 pages.
Lap-Band APTM, "System with Adjustable Gastric Banding system with Omniform Design", Product Brochure, Jul. 2007, 16 pages.
Lap-Band® "Adjustable Gastric Banding System" by BioEnterics Corporation, Product Brochure, 12 pages.
Lap-Band® System Fact Sheet, @2007 Allergan, Inc., 2 pages.
Medcomp, "PortCT Technology", display at SIR Conference, Toronto, Canada, Mar. 2006, 1 page.
International Search Report and Written Opinion received for PCT Patent Application No. PCT/US2007/011456, dated Aug. 28, 2008, 6 pages.
International Search Report and Written Opinion received for PCT Patent Application No. PCT/US2008/010520, dated Feb. 24, 2009, 6 pages.
International Search Report Received for for PCT Application No. PCT/US2006/015695, dated Jan. 11, 2007, 6 pages.
"International Search Report Received for PCT Application No. PCT/US2006/008022", dated Jul. 5, 2006, 2 pages.
"International Search Report Received for PCT Application No. PCT/US2007/006776", dated Dec. 18, 2007, 1 page.
"International Search Report Received for PCT Application No. PCT/US2007/011015", dated Jun. 10, 2008, 2 pages.
"International Search Report Received for PCT Application No. PCT/US2008/067679", dated Sep. 30, 2008, 3 pages.
"International Search Report Received for PCT Application No. PCT/US2008/070330", dated Dec. 1, 2008, 5 pages.
"International Search Report Received for PCT Application No. PCT/US2008/070345", dated Dec. 1, 2008, 5 pages.
International Search Report Received for PCT Patent Application No. PCT/US1999/028695, dated Apr. 11, 2000, 2 pages.
International Search Report Received for PCT Patent Application No. PCT/US2009/062854, dated Dec. 23, 2009, 2 pages.
PCT Request received for PCT Application No. PCT/US2008/67679, filed on Dec. 24, 2008, 4 pages. (E3 Opposition / EP 2164559).
"Written Opinion Received for PCT Application No. PCT/US2006/015695", dated Oct. 30, 2007, 8 pages.

"Written Opinion Received for PCT Application No. PCT/US2006/49007", dated Oct. 1, 2007, 4 pages.
"Written Opinion Received for PCT Application No. PCT/US2007/006776", dated Dec. 18, 2007, 3 pages.
"Written Opinion Received for PCT Application No. PCT/US2007/011015", dated Jun. 10, 2008, 3 pages.
"Written Opinion Received for PCT Application No. PCT/US2007/011456", dated Aug. 28, 2008, 4 pages.
"Written Opinion Received for PCT Application No. PCT/US2008/010520", dated Feb. 24, 2009, 4 pages.
"Written Opinion Received for PCT Application No. PCT/US2008/067679", dated Sep. 30, 2008, 4 pages.
"Written Opinion Received for PCT Application No. PCT/US2008/070330", dated Dec. 1, 2008, 5 pages.
"Written Opinion Received for PCT Application No. PCT/US2008/070345", dated Dec. 1, 2008, 6 pages.
Plinski, et al., "Implantable Cardioverter-Defribillators: Implications for the Nonelectrophysiologist", Annals of Internal Medicine, Abstract of vol. 122, No. 10, pp. 770-777, May 15, 1995, 3 pages.
Port-A-Cath®, "Many Port-A-Cath® System Choices", Product Brochure, SIMS Deltec, Inc., 1996, 5 pages.
Port-A-Cath®, "Single-lumen Implantable Vascular Access Systems", Product Specifications Smith Medical, 2004, 4 pages.
Rappolt, et al., "Radiopaque Codification and X-ray identification of Ingested Drugs", Ingestive Radioiogy, May-Jun. 1966, 4 pages.
Salis, et al., "Maximal Flow Rates Possible during Power Injection through Currently Available PICCs: An In-Vitro Study", Journal of the Association for Vascular Access, vol. 15, No. 3, Mar. 2004, pp. 275-281.
Sandstede, Joern, "Pediatric CT", available online at <www.multislice-ct.com, MultiSLICE-CT.com>, version 02, May 2, 2003, 36 pages.
Sanelli, et al., "Safety and Feasibility of Using a Central Venous Catheter for Rapid Contrast Injection Rates", American Journal of Radiology, vol. 183, pp. 1829-1834, Dec. 2004, 6 pages.
Sawyer, Dick, "Do It by Design: An Introduction to Human Factors in Medical Devices", U.S. Department of Health and Human Services, Public Health Service, Food and Drug Administration, Center for Devices and Radiological Health, Dec. 1996, 55 pages.
Shah, Tilak M., "Radiopaque Polymer Formulations for Medical Devices", Medical Device and Diagnostic Industry, Mar. 2000, 6 pages.
Smith, Lisah, "Implanted Ports, Computer Tomography, Power Injectors, and Catheter Rupture", Clinical Journal of Oncology Nursing, vol. 12, No. Oct. 5, 2008, 4 pages.
Solomon,, et al., "CIN Strategies: Anticipate, Manage, Prevent", Supplement to Imaging Economics, May 2007, 20 pages.
Steinbach, et al., "Breast Implants, Common Complications, and Concurrent Breast Disease", RadioGraphies, vol. 13, No. 1, pp. 95-118, 1993, 24 pages.
Stevens, et al., "A Randomized, Prospective Trial of Conventional Vascular Ports vs. The Vortex "Clear-Flow" Reservoir Port in Adult Oncology Patients", The Journal of Vascular Access Devices, 2000, pp. 37-40.
Sullivan, et al., "Radiopaque Markers on Mammary Implants", American Journal of Roentgenology 153(2):428, 2 pages.
Cardiovascular and Interventional Radiology, Review Article, "Central Venous Access Catheters: Radiological Management of Complications," by U.K. Teichgraber et al., published online Jul. 31, 2003, 13 pages.
Thistlethwaite et al., "Generalized Feature-Based RSA of Orthopaedic Implants," 2003 Summer Bioengineering Conference, Jun. 25-29, Sonesta Beach Resort in Key Biscayne, Florida, 2 pages.
U.S. Food and Drug Administration, "Guidance for Institutional Review Boards and Clinical Investigators 1998 Update: Medical Devices." Version Sep. 10, 2008, 13 pages.
Urquiola, Javier, et al., "Using Lead Foil as a Radiopaque Marker for Computerized Tomography Imaging When Implant Treatment Planning," The Journal of Prosthetic Dentistry, vol. 77, No. 2, Feb. 1997, pp. 227-228.
Williamson, et al., "Assessing the Adequacy of Peripherally Inserted Central Catheters for Power Injection of Intravenous Contrast Agents for CT", Journal of Computer Assisted Tomography, vol. 6, No. 6, 2001, pp. 932-937.

(56) References Cited

OTHER PUBLICATIONS

Vergara, et al., "Adverse Reactions to Contrast Media in CT: Effects of Temperature and Ionic Property", Radiology, vol. 199, No. 2, May 1996, 4 pages.
Vogelzang, Robertl, "Power Injection Through Central Venous Catheters: Physiological and Hemodynamic Considerations", The McGaw Medical Center of Northwestern University, Feinberg School of Medicine, 3 pages.
Wells, S. "Venous Access in Oncology and Haematology Patients: Part One." Nursing Standard, vol. 22, No. 52, pp. 39-46, Sep. 3, 2008, 9 pages.
Funaki, "Central Venous Access: A Primer for the Diagnostic Radiologist", 2002, AJR, 179:309-318.
Cope et al., Access Device Guidelines—Recommendations for Nursing Practice and Education, 2d Edition, 2004, 85 pages.
Gebauer et al., "Contrast Media Power Injection Using Central-Venous Port Catheters—Results of an In Vitro Study", Experimental Radiology, 2005, 177:1417-1423.
"Radiopaque Imprinting Enables Alternative to Angioplasty", Medical Product Manufacturing News, Apr. 2003, 1 page.
McKillop et al., "Retained Surgical Swab Misinterpreted as Epicardial Pacing Wire on Chest X Ray", 1996, Heart, 75:342.
Wolfson et al., "Imaging of Surgical Paraphernalia: What Belongs in the Patient and What Does Not", 2000, Radiographics, 20:1665-1673.
O'Connor et al., "Imaging of Retained Surgical Sponges in the Abdomen and Pelvis", 2003, AJR, 180:481-489.
Walter et al., "Radiographic Identification of Commonly Used Implanted Pacemakers", The New England Journal of Medicine, 1969, vol. 281, 22:1230-1231.
Walter, "Radiographic Identification of Commonly Used Pulse Generators—1970", 1971, JAMA, vol. 215, 12:1974-1975.

\* cited by examiner

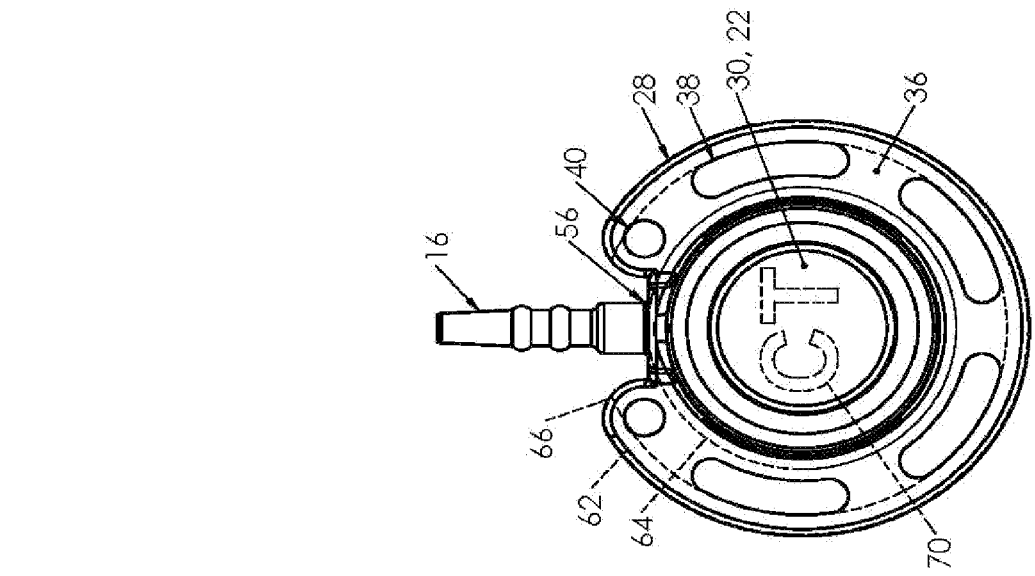
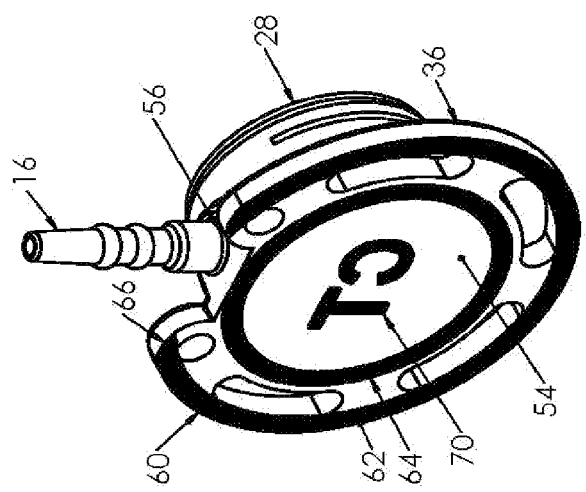
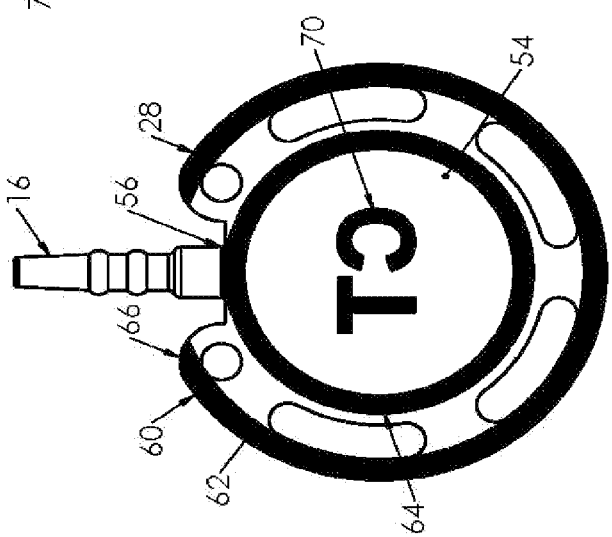

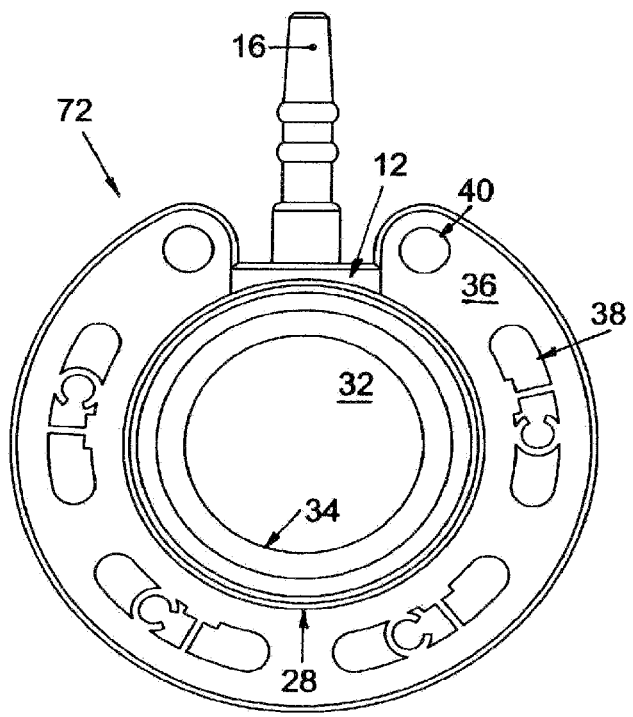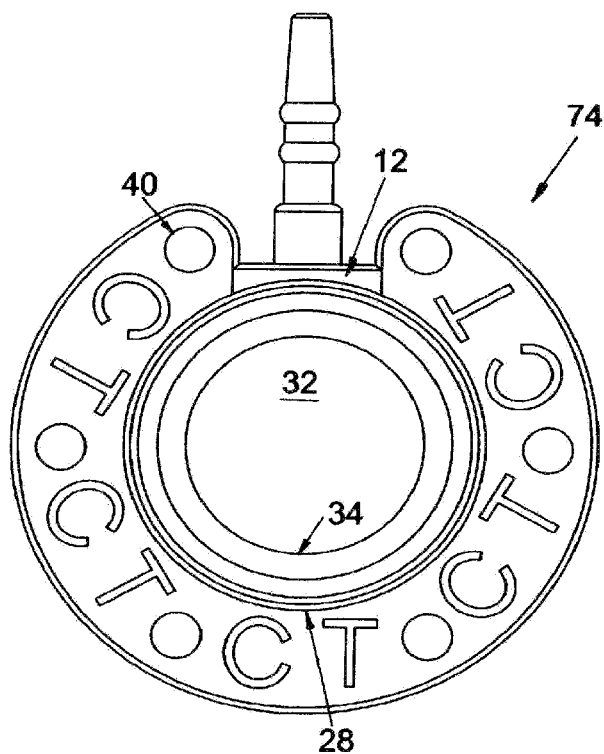
FIG. 11

VENOUS ACCESS PORT WITH MOLDED AND/OR RADIOPAQUE INDICIA

RELATED APPLICATIONS

This application is a continuation of, and claims the benefit of, co-pending U.S. patent application Ser. No. 16/035,879, filed Jul. 16, 2018, which is a divisional of U.S. patent application Ser. No. 15/350,273, filed Nov. 14, 2016, which is a continuation of U.S. patent application Ser. No. 13/550,745, filed Jul. 17, 2012, now U.S. Pat. No. 9,533,133, which is a continuation of U.S. patent application Ser. No. 12/143,377, filed Jun. 20, 2008, now U.S. Pat. No. 8,257,325, which claims the benefit of U.S. provisional application No. 60/936,491, filed Jun. 20, 2007, which applications are incorporated herein by reference.

FIELD OF THE INVENTION

This invention relates generally to medical devices, and more particularly to venous access ports having integrally molded and/or radiopaque indicia.

BACKGROUND OF THE INVENTION

Venous access ports for the infusion and/or withdrawal of fluids from a patient are well-known, secured to the proximal end of an implanted catheter. These ports are typically used for drug infusion or for withdrawal of small amounts of blood, where large flows of fluid are not required. The ports are assemblies of a needle-impenetrable housing with a discharge port in fluid communication with a catheter and a reservoir within the port housing, and provide as subcutaneous self-sealing septum that defines an access site for multiple needle sticks through the covering skin tissue of the patient, through the septum, and into the reservoir, without the need to continuously search for new access sites. Examples of such ports are disclosed, for example, in U.S. Pat. Nos. 4,704,103; 4,762,517; 4,778,452; 5,185,003; 5,213,574; and 5,637,102.

It is desired to provide a venous access port assembly that provides a medical practitioner with the capability to discern an important property of the port assembly after the port assembly has been implanted into a patient.

BRIEF SUMMARY OF THE INVENTION

The present invention is directed to an implantable venous access port having a marking visible by X-ray examination, providing identification on the X-ray of characteristics of the implanted access port. These characteristics might otherwise be unknown once the port is implanted under the skin of the patient. Considering that X-ray examination is normal practice prior to medical access of the port, an X-ray examination that also identifies important characteristics of an implanted port is beneficial to the practitioner.

Accordingly, one aspect of the present invention is the incorporation of a molded marking into or onto the venous access port, or the addition of radiopaque indicia onto the access port, and/or the addition of radiopaque indicia onto a molded marking integrated into the access port, all of which would be discernable under X-ray examination to provide information concerning a characteristic or attribute of the venous access port, so that a practitioner, subsequent to implantation of the access port under the skin of a patient, can determine that characteristic or attribute of the port by X-ray examination.

One such characteristic could be power injectable capability; that is, an indication that the venous access port is rated for the power injection of contrast fluid. Power injection capability can be indicated with the letters "CT," for "computed tomography," or "contrast enhanced computed tomography." "CT" would indicate the access port's capability to withstand high pressures used during injection of contrast fluid into a patient, and the letters "CT" would be understood in medical practice to indicate that the port is suitable for the high pressure injection of contrast fluid. Naturally, any characteristic or attribute of the venous access port could be indicated, and any choice of letters or symbols could be employed.

In one embodiment, an access port of the present invention includes a housing and a septum, providing an interior reservoir and a passageway extending from the reservoir through a stem of a discharge port to establish fluid communication with a proximal end of a catheter lumen to which the port assembly is secured prior to placement of the assembly into a patient. The port may optionally have more than one reservoir and associated septum. The housing could include molded therein the letters "CT." If the housing is made of a plastic material, such as a silicone elastomer the letters "CT" (or the entire housing) could be loaded with a radiopaque agent, allowing the letters "CT" (or the cadre housing to be seen by X-ray examination. If the housing comprises a metal material, or if the portion of the housing including the letters "CT" is made of a metal material, the letters would naturally be visible by X-ray examination.

BRIEF DESCRIPTION OF THE DRAWINGS

The accompanying drawings, which are incorporated herein and constitute part of this specification, illustrate the presently preferred embodiments of the invention, and together with the general description given above and the detailed description given below, serve to explain the features of the invention. In the drawings;

FIG. 8 is an isometric view from below of one embodiment of the housing base of FIG. 5, showing radiopaque indicia applied on the housing base bottom surface;

FIGS. 9 and 10 are bottom and top views of the housing base of FIG. 8 having radiopaque indicia thereon, with the top view (FIG. 10) being analogous to a X-ray view of the venous access port seen by a radiologist, with indicia visible by X-ray shown by dashed lines in FIG. 10;

FIG. 11 illustrates top views of two alternative embodiments of the needle-impenetrable housing base of the venous access port of FIG. 1, showing integrally molded "CT" markings;

DETAILED DESCRIPTION OF THE INVENTION

Figure 1:
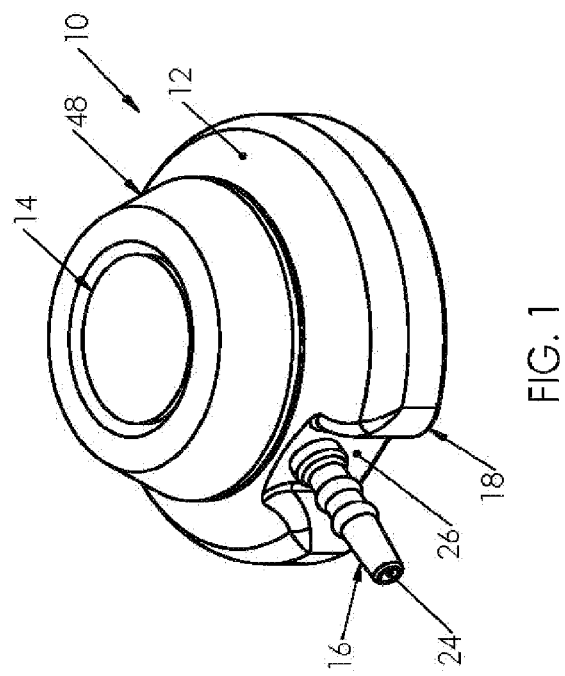
FIG. 1 is an isometric view of one embodiment of a venous access port of the present invention.
Figure 2:
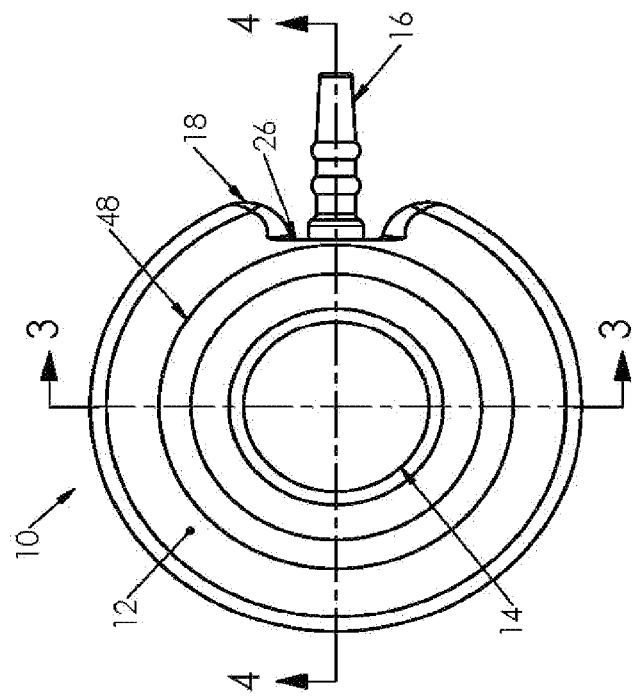
FIG. 2 is a pan view of the port FIG. 1.

Certain terminology is used herein for convenience only and is not to be taken as a limitation on the present invention. The terms "distal" and "proximal" refer, respectively, to directions closer to and away from the insertion tip of a catheter in an implantable catheter assembly. The terminology includes the words specifically mentioned, derivatives thereof, and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Venous access port assembly 10 of FIGS. 1 to 4 includes a housing 12 and a septum 14, with a discharge port 16 extending from a distal end 18 of the port assembly 10 to be attached securely and sealingly to the proximal end of a catheter (not shown). A passageway 20 extends from the interior reservoir 22 to the distal tip opening 24 of discharge port 16. A recess 26 is seen to be provided along both sides of discharge port 16, facilitating insertion of the discharge port 16 into the catheter lumen and providing a clearance for a locking sleeve or clamp (not shown) utilized to compress the catheter lumen wall against the exterior surface of the discharge port 16 for assured sealed connection of the catheter with the port assembly 10.

With reference now to FIGS. 3 to 7, the interior of the port assembly 10 is shown to provide an interior reservoir 22. Housing 12 is shown to include a housing base 28 of needle-impenetrable material that includes a web 30 having a bottom boor 32 and side walls 34 that define the interior reservoir 22 beneath septum 14. Bottom floor 32 may be convex or elevated (not shown) toward the center of the reservoir, if desired. Housing base 28 includes a base flange 36 extending radially outwardly from the bottom of well 30, and base flange 36 includes openings 38, 40 that serve to enable suturing to the patient upon placement of the venous access port and the attached catheter into the patient.

Figure 3:
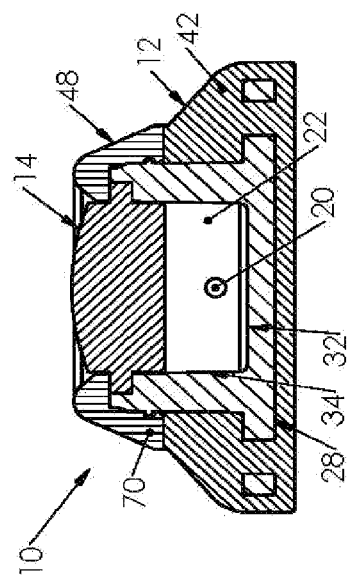
FIGS. 3 and 4 are cross-sectional views of the port of FIGS. 1 and 2 taken along lines 3-3 and lines 4-4 of FIG. 2, respectively.
Figure 4:
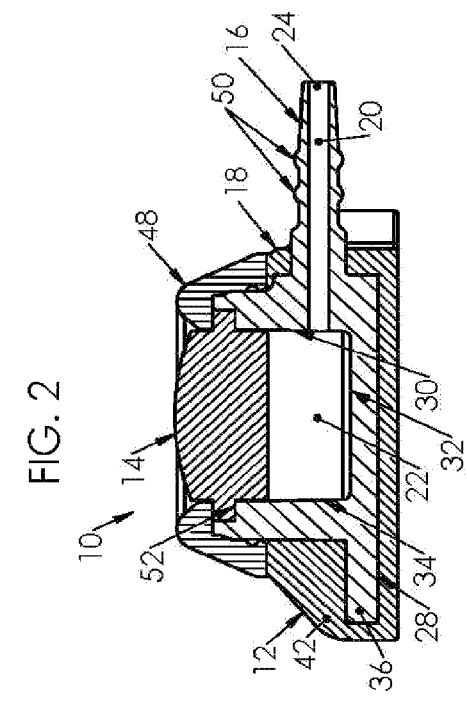

As shown in FIGS. 3 and 4, a skirt 42 is overmolded about housing base 28 and may be of silicone elastomer. It is seen that skirt 42 encapsulates the outer surfaces of the bottom wall 44 and the bottom portion of the side walls 46 of housing base 28, and is shown to fill in the suture holes 38, 40; but since the material is silicone elastomer, suturing is possible since the suturing needle can easily be inserted through the material of skirt 42 and through the suture holes, and thereafter the filled openings provide minimal opportunity for ingrowth of patient tissue into the openings.

Figure 7:
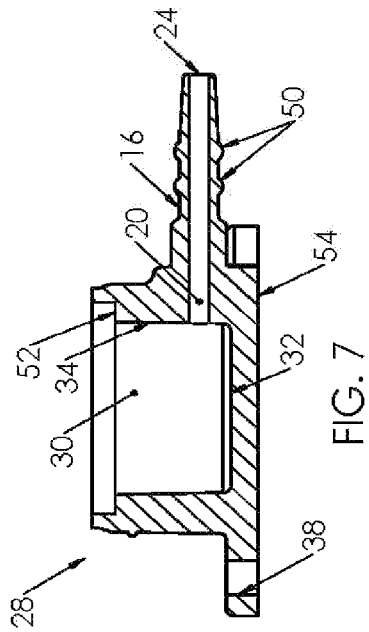
FIGS. 6 and 7 are transverse cross-sectional and longitudinal cross-sectional views of the housing base of FIG. 5.
Figure 5:
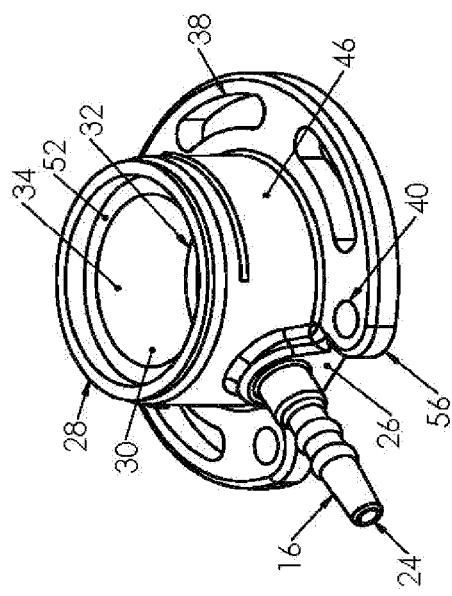
FIG. 5 is an isometric view of a needle-impenetrable housing base of the venous access port of FIG. 1.
Figure 6:
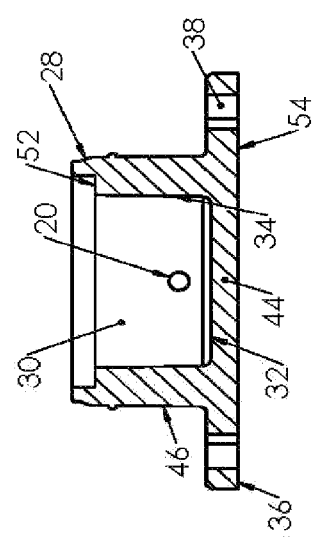

Also seen in FIGS. 1 to 4 is cap 48, which secures to housing base 28 to in turn secure septum 14 in position in the port assembly 10. Preferably, skirt 42 is insert molded onto base flange 36 of housing base 28 after cap 48 is secured to the upper portion of housing base 28 to secure the septum in position. It is seen in FIGS. 4 and 7 that discharge port 16 is integral with housing base 28 as is preferable. Discharge port 16 is shown to have a pair of annular ridges 50 that facilitate with the mechanical connection of the catheter proximal end with the port assembly 10. Housing base 28 includes a septum seat 52 extending into the top of well 30, into which a flange of the septum will be seated, preferably under radially inward compression. Housing base 28 has a bottom outer surface 54.

Radiopaque markings 60 of the present invention are shown in FIGS. 8 to 10. A larger outer circle 62 is seen provided on the outermost periphery of bottom base surface 54, and a smaller inner circle 64 is seen provided within the area circumscribed by the suture openings 38 and holes 40 through base flange 36. Adjacent to discharge port 16, a recess 56 is provided in the skirt of the housing base to provide a clearance for use of a connection sleeve that will be used to secure the catheter (not shown), and outer circle 62 is shown to have a gap 66 at the recess. Outer and inner circles or rings 62, 64 circumscribe radiopaque indicia 70.

Radiopaque indicia 70 are provided on bottom outer surface 54 within the region directly beneath the reservoir and septum. In the example shown, indicia 70 comprise the letters "CT" (FIG. 10) representing the term "computed tomography." The meaning of this particular example of indicia is that the venous access port assembly 10 is rated for high pressure injection such as is necessary for infusion into the patient of contrast medium that is used in computed tomography. Other indicia may of course be used that indicate some other attribute or characteristic of the venous access port assembly. The radiopaque markings and indicia would appear on an X-ray of the patient, and the indicia are provided in a mirror-image orientation on the bottom outer surface of the housing base (FIGS. 7 and 8) so that the indicia would appear as "CT" when the X-ray is viewed (FIG. 9), easily discerned by the radiologist or technologist. Centering of the indicia within the region (identified as "30, 22" in FIG. 10) directly beneath the reservoir and septum minimizes any obscuring by the structure of the venous access port assembly, and the indicia may also be easily discernable should the port assembly be at an angle from the horizontal plane of the X-ray; the outer and inner circles 62, 64 would appear oval or elliptical should the port assembly be at such an angle. Gap 66 in outer circle 62 would also appear and would indicate the location of the discharge port stem 16, The radiopaque markings may constitute marking fluid that is embossed or imprinted or otherwise applied onto the surface of the housing base 28, such as black radiopaque ink Part No. C11002 Rev A formulated by Creative Imprinting of Erie, Pa., from Marabu Tampapur TPU 910 clear with tungsten added, available from Marabuwerke GmbH & Co. KG of Stuttgart, Germany, and may be applied on plasma-treated surfaces. At least the housing base 28, the septum 14 and the skirt 42 are of radiotransparent or radiolucent material as is well known in implanted medical devices, and the housing base may be molded of polysulfone resin.

The radiopaque markings may alternatively applied to the inwardly facing surface of the bottom wall of the housing base, or may constitute foil or film (such as a decal) of radiopaque material embedded within the housing base, these alternatives not being shown in the drawings.

Figure 12:
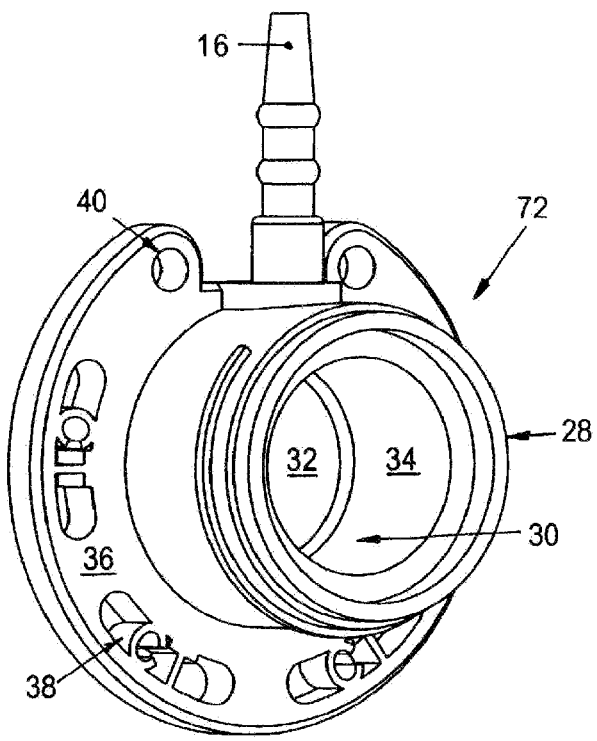
FIG. 12 illustrates an isometric view of one of the FIG. 11 embodiments of the needle-impenetrable housing base of the venous access port of FIG. 1, featuring an integrally molded "CT" marking where the letters "CT" are formed of housing material.
Figure 13:
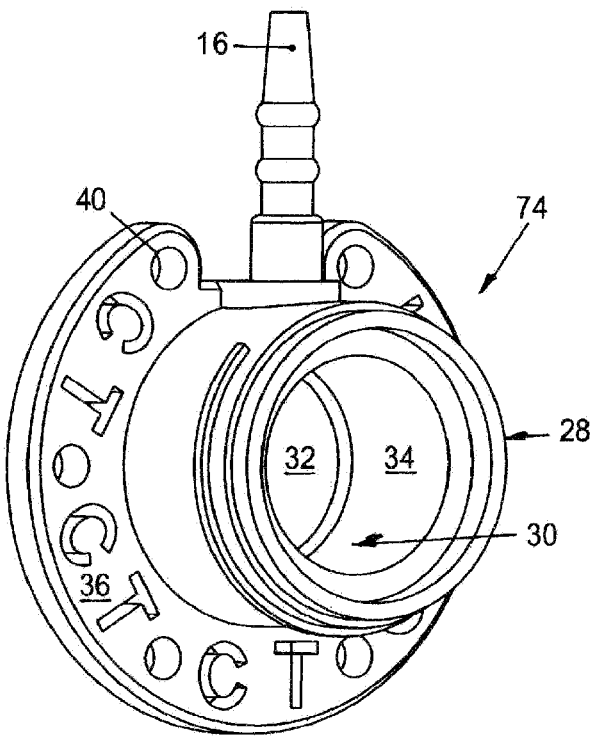
FIG. 13 illustrates an isometric view of the other of the FIG. 11 embodiments of the needle-impenetrable housing base of the venous access port of FIG. 1, featuring an integrally molded "CT" marking where the letters "CT" comprise voids in the housing material, as if cut or punched out of the housing material.

FIG. 11 illustrates top views of two alternative embodiments 72, 74 of the needle-impenetrable housing base 28 of the venous access port 10 of the present invention. Each of the alternative embodiments 72, 74 shows "CT" markings integrally formed in the base flange 36 of the housing base 28. The first alternative embodiment 72, an isometric view of which is illustrated in FIG. 12, features integrally molded "CT" markings within the suture openings 38, where the letters "CT" are formed of the base flange 36 material. The second alternative embodiment 74, an isometric view of which is illustrated in FIG. 13, features integrally molded "CT" markings alongside the suture openings 38, 40, where the markings are voids in the base flange 36 material, as if cut or punched out of the base flange 36 material. Naturally, the markings could be configured elsewhere within or about the housing base 28, or within a peripheral portion of another component of the venous access port 10.

If the housing base 28 is made of a plastic material, such as a silicone elastomer or polysulfone resin, the letters "CT," or the base flange 36, or the entire housing base 28, could be applied with a radiopaque agent or fluid, allowing the applied area to be visible by X-ray examination. If the housing base 28 is comprised of a metal material, or if the base flange 36, or a portion thereof, is comprised of metal (particularly the letters "CT"), those portions would naturally be visible by X-ray examination without application of the radiopaque agent.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A venous access port assembly for implantation into a patient, comprising:
    a needle-penetrable septum;
    a housing comprising a housing base at least partially defining at least one reservoir; and
    a peripheral component external to the housing, the peripheral component comprised at least partially of a radiopaque material, wherein:
        the peripheral component includes one or more X-ray discernable voids extending through a height of the peripheral component,
        the one or more X-ray discernable voids indicating under X-ray examination that the venous access port assembly is capable of withstanding pressures used during injection of contrast fluid.

2. The venous access port assembly of claim 1, wherein the peripheral component is integral with and extends outwardly from the housing.

3. The venous access port assembly of claim 1, wherein the peripheral component extends substantially about a perimeter of the housing.

4. The venous access port assembly of claim 1, further comprising a radiotransparent or radiolucent skirt overmolded about at least a portion of the housing.

5. The venous access port assembly of claim 1, further comprising a radiotransparent or radiolucent skirt overmolded about the peripheral component.

6. The venous access port assembly of claim 1, wherein the one or more X-ray discernable voids extend completely through the peripheral component.

7. The venous access port assembly of claim 1, wherein the housing further comprises a cap.

8. The venous access port assembly of claim 1, wherein the one or more X-ray discernable voids are shaped as letters or symbols capable of indicating an orientation of the venous access port assembly after implantation.

9. A venous access port assembly for implantation into a patient, comprising:
    a needle-penetrable septum;
    a housing comprising a housing base at least partially defining at least one reservoir; and
    a peripheral component external to the housing, the peripheral component comprised at least partially of a radiopaque material, wherein:
        the peripheral component includes one or more X-ray discernable voids extending through a height of the peripheral component,
        the one or more X-ray discernable voids are visible under X-ray examination, and
        the one or more X-ray discernable voids are in the shape of letters "CT".

10. The venous access port assembly of claim 9, wherein the peripheral component is integral with and extends outwardly from the housing.

11. The venous access port assembly of claim 9, wherein the peripheral component extends substantially about a perimeter of the housing.

12. The venous access port assembly of claim 9, further comprising radiotransparent or radiolucent skirt overmolded about at least a portion of the housing.

13. The venous access port assembly of claim 9, further comprising a radiotransparent or radiolucent skirt overmolded about the peripheral component.

14. The venous access port assembly of claim 9, wherein the one or more X-ray discernable voids extend completely through the peripheral component.

15. The venous access port assembly of claim 9, wherein the one or more X-ray discernable voids indicate, under X-ray examination, that the venous access port assembly is capable of withstanding pressures used during injection of contrast fluid.

16. The venous access port assembly of claim 9, wherein the housing further comprises a cap.

17. The venous access port assembly of claim 9, wherein the one or more X-ray discernable voids indicate an orientation of the venous access port assembly after implantation.

* * * * *